United States Patent
Baba et al.

(10) Patent No.: US 7,515,689 B2
(45) Date of Patent: Apr. 7, 2009

(54) X-RAY MEASURING INSTRUMENT

(75) Inventors: Rika Baba, Kokubunji (JP); Ken Ueda, Ome (JP)

(73) Assignee: Hitachi Medical Corporation, Tokyo (JP)

(*) Notice: Subject to any disclaimer, the term of this patent is extended or adjusted under 35 U.S.C. 154(b) by 90 days.

(21) Appl. No.: 11/722,802

(22) PCT Filed: Dec. 8, 2005

(86) PCT No.: PCT/JP2005/022522

§ 371 (c)(1), (2), (4) Date: Jun. 26, 2007

(87) PCT Pub. No.: WO2006/080144

PCT Pub. Date: Aug. 3, 2006

(65) Prior Publication Data
US 2008/0043900 A1  Feb. 21, 2008

(30) Foreign Application Priority Data
Jan. 27, 2005  (JP) .............................. 2005-019285

(51) Int. Cl.
*G21K 3/00* (2006.01)
(52) U.S. Cl. .......................... 378/156; 378/4; 378/18; 378/207
(58) Field of Classification Search .................. 378/4, 378/156, 207
See application file for complete search history.

(56) References Cited

U.S. PATENT DOCUMENTS

| | | | | |
|---|---|---|---|---|
| 3,755,672 A * | 8/1973 | Edholm et al. | ............... | 378/158 |
| 6,418,193 B1 * | 7/2002 | Albagli | ........................ | 378/158 |
| 6,438,197 B2 * | 8/2002 | Stierstorfer | ..................... | 378/8 |
| 6,633,627 B2 * | 10/2003 | Horiuchi | ...................... | 378/156 |
| 6,735,273 B2 * | 5/2004 | Flohr et al. | ..................... | 378/5 |
| 6,990,171 B2 * | 1/2006 | Toth et al. | ...................... | 378/16 |

FOREIGN PATENT DOCUMENTS

| | | |
|---|---|---|
| JP | 2003-339686 | 12/2003 |
| JP | 2004-305349 | 11/2004 |

OTHER PUBLICATIONS

Glick et al., Evaluating the impact of x-ray spectral shape on image quality in flat-panel CT breast imaging, Med Phys, 34, (1), Jan. 2007, pp. 5-24.*

* cited by examiner

*Primary Examiner*—Edward J Glick
*Assistant Examiner*—Alexander H Taningco
(74) *Attorney, Agent, or Firm*—Antonelli, Terry, Stout & Kraus, LLP.

(57) ABSTRACT

An X-ray measuring instrument in which an object under examination is irradiated with X-rays, measurement data on the object is detected, a filter for adjusting the amount of transmitted X-rays is disposed between an X-ray source and the object, the relative position of the X-ray source to the object is varied, and the acquired measurement data is computed. The measurement data is subjected to logarithm transform to acquire projection data, and the amount of absorbed X-rays of the filter corresponding to the acquired projection data is determined. The thickness of the filter is computed by using a predetermined transform formula for the acquired amount of absorbed X-rays. A correction coefficient corresponding to the projection data acquired from the computed thickness of the filter is determined, and the projection data is multiplied by the determined correction coefficient. The projection data multiplied by the correction coefficient is restructure-computed to obtain a three-dimensional image.

17 Claims, 4 Drawing Sheets

FIG.2

| v \ u | 1 | 2 | ... | $N_u$ |
|---|---|---|---|---|
| 1 | $A_f(1,1)$ | $A_f(2,1)$ | ... | $A_f(N_u,1)$ |
| 2 | $A_f(1,2)$ | $A_f(2,2)$ | ... | $A_f(N_u,2)$ |
| ... | ... | ... | | ... |
| $N_v$ | $A_f(1,N_v)$ | $A_f(2,N_v)$ | ... | $A_f(N_u,N_v)$ |

FIG.3

| $A_s$ \ $E_f$ | 0 | 1 | ... | $E_{max}$ |
|---|---|---|---|---|
| 0.00 | $G(0,0.00)$ | $G(1,0.00)$ | ... | $G(E_{max},0.00)$ |
| 0.01 | $G(0,0.01)$ | $G(1,0.01)$ | ... | $G(E_{max},0.01)$ |
| 0.02 | $G(0,0.02)$ | $G(1,0.02)$ | ... | $G(E_{max},0.02)$ |
| ... | ... | ... | | ... |
| $S_{max}$ | $G(0,S_{max})$ | $G(1,S_{max})$ | ... | $G(E_{max},S_{max})$ |

FIG.4
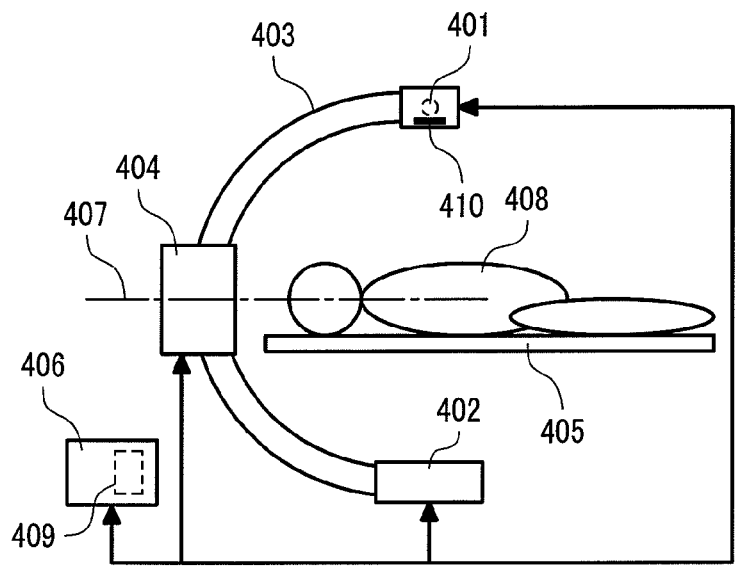
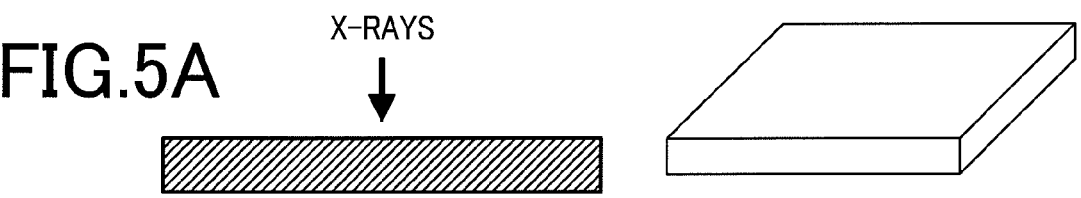
FIG.5A
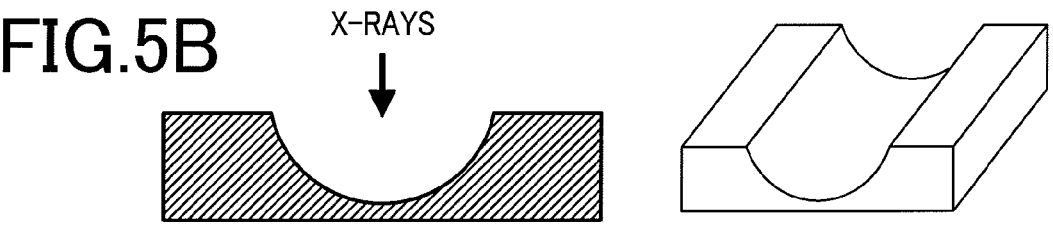
FIG.5B
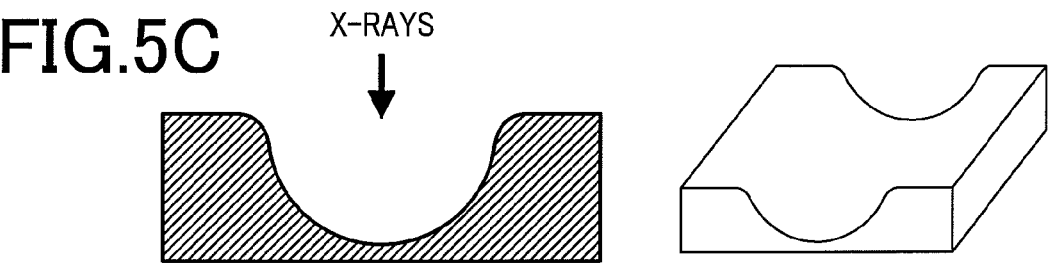
FIG.5C

X-RAYS

X-RAY MEASURING INSTRUMENT

TECHNICAL FIELD

The present invention relates to an X-ray measuring instrument capable of producing an excellent three-dimensional image that has the uniformity of values improved by suppressing the saturation of a detector.

BACKGROUND ART

There is an X-ray measuring instrument having an X-ray source and a two-dimensional detector disposed at the open ends of a support shaped like letter C (hereinafter referred to as a C-arm) so that the X-ray source and two-dimensional detector will be opposed to each other. There is a structure that suspends the C-arm from the ceiling or a structure that bears the C-arm on the floor. Moreover, there is an X-ray measuring instrument having the X-ray source and two-dimensional detector mounted in a gantry in such a manner that the X-ray source and two-dimensional detector are opposed to each other. In these instruments, while the pair of the X-ray source and detector is rotated about a subject by rotating the C-arm or gantry, X-ray measurement can be performed. Moreover, multiple measurement data items acquired during rotational measurement are corrected in order to produce a set of projection data items required for three-dimensional reconstruction. A three-dimensional reconstruction algorithm is used to perform reconstruction on the set of projection data items, whereby a three-dimensional image can be produced. The three-dimensional measurement is described in non-patent document 1.

Non-patent document 1: New Medicine, October 2002, Vol. 29, No. 10, pp. 102-105

DISCLOSURE OF THE INVENTION

Problem to be Solved by the Invention

In conventional X-ray measuring instruments, when a thick subject is measured, an X-ray dose reaching a detector after being transmitted by the subject is limited, and the quality of a measured X-ray image is degraded. When the X-ray dose reaching the detector is increased by intensifying the exposure of X-rays irradiated from an X-ray source or decreasing the distance between the X-ray source and detector, the image quality relevant to a subject area can be improved. On the other hand, as far as an area where the subject is not present or an area where the thin portion of the subject is present is concerned, the exposure of X-rays reaching the detector is increased. In detector elements in which the exposure of X-rays exceeds a detectable limit, a saturation phenomenon takes place. This causes the detector elements to fail to indicate a correct value. For suppression of the saturation of the detector, when a filter made of a metal or the like is interposed between the X-ray source and subject, the energy distribution of X-rays incident on the subject varies depending on the type of filter or the thickness thereof. When an X-ray image showing a different energy distribution is used for reconstruction, a produced three-dimensional image does not express correct values.

Moreover, in the case where no filter is disposed or the types of filters or the thicknesses thereof are even, the energy distribution of X-rays incident on a subject is uniform. While X-rays are being transmitted by the subject, the energy distribution of X-rays varies depending on the type of subject or the thickness thereof. When an X-ray image showing a different energy distribution is used for reconstruction, a produced three-dimensional image does not express correct values.

Moreover, scattered X-rays caused by a filter or a subject fall on a detector and coexist with data. When an X-ray image affected by the coexisting scattered X-rays is used for reconstruction, a produced three-dimensional image does not express correct values.

Accordingly, an object of the present invention is to provide an X-ray measuring instrument capable of producing an excellent three-dimensional image by correcting the non-uniformity in values of a three-dimensional image.

Means for Solving Problem

The above object is accomplished with an X-ray measuring instrument including: an X-ray source that generates X-rays to be irradiated to an object; an X-ray detector that is opposed to the X-ray source with the object between them and that detects as measurement data X-rays transmitted by the object; a filter that is interposed between the X-ray source and object and regulates the exposure of X-rays to be transmitted; a holding unit that holds the X-ray source and X-ray detector; a rotating unit that rotates the X-ray source and X-ray detector about the object; and a control processing unit that computes measurement data items which are detected by the X-ray detector at multiple angles with respect to the object that is rotated by the rotating unit. The control processing unit logarithmically converts measurement data so as to produce projection data, obtains an X-ray absorption coefficient relevant to the filter using the produced projection data, calculates the thickness of the filter by applying a predetermined conversion expression to the obtained X-ray absorption coefficient, obtains a correction coefficient for the produced projection data according to the calculated thickness of the filter, multiplies the projection data by the obtained correction coefficient, computes the projection data, which is multiplied by the correction coefficient, for reconstruction, and thus produces a three-dimensional image.

Effect of the Invention

According to the present invention, a three-dimensional image unaffected by a saturation phenomenon in X-ray detector elements, a change in an energy distribution caused by a filter or a subject, or scattered X-rays caused by the filter or subject can be produced.

BEST MODE FOR CARRYING OUT THE INVENTION

FIG. 4 is a conceptual diagram showing in a sectional form a side view of an example of an X-ray measuring instrument to which the present invention is applied. The X-ray measuring instrument includes an X-ray source 401, a detector 402, a support 403, a rotating unit 404, a table 405, and a control processing unit 406. The X-ray source 401 and detector 402 are mounted in the support 403. An arm shaped like letter C, an arm shaped like a bracket, or a gantry is adopted as the support 403. In FIG. 4, the support 403 is the arm shaped like letter C. A form in which the support 403 is suspended from the ceiling or a form in which the support 403 is borne on the floor is conceivable. The support 403 is rotated about a subject 408, who lies down on the table 405, with an axis of rotation 407 as a center by the rotating unit 404.

In FIG. 4, a form in which the axis of rotation 407 and table 405 are parallel to the floor is shown as the most typical form.

By moving the support 403 and table 405, the axis of rotation 407 can be defined obliquely to a body axis. Moreover, it is possible to establish a form in which the axis of rotation 407 is perpendicular to the floor and the support 403 is rotated about the subject 408 who is standing or seated.

In FIG. 4, the X-ray source 401 and detector 402 are rotated about the subject 408 with the axis of rotation 407 as a center by the rotating unit 404. The X-ray source 401 and detector 402 may remain stationary, and the subject 408 may be rotated with the axis of rotation 407 as a center by the rotating unit 404. Otherwise, the X-ray source 401, detector 402, and subject 408 may be rotated with the axis of rotation 407 as a center. In any case, the rotation is regarded as a relative rotary motion, and rotational measurement is performed in the same manner.

A flat-panel detector, a combination of an X-ray image intensifier and a CCD camera, an imaging plate, a CCD detector, or a solid-state detector is adopted as the detector 402. As the flat-panel X-ray detector, pairs of a photodiode and an amorphous silicon TFT that are arranged in the form of a square matrix and directly combined with a fluorescent substance will do.

X-rays generated by the X-ray source 401 are transmitted by the subject 408, converted into electric signals proportional to X-ray intensities by the detector 402, and transferred as measurement data to the control processing unit 406. The control processing unit 406 controls X-ray generation by the X-ray source 401, data acquisition by the detector 402, and rotation of the support 403 by the rotating unit 404. Consequently, the X-ray measuring instrument can perform rotational measurement in which while the support 403 is rotated, X-rays are generated and measurement data is acquired. The control processing unit 406 executes a logarithmic conversion process and a reconstructive computation process for measurement data so as to produce three-dimensional data. In FIG. 4, the control processing unit 406 is disposed outside the detector 402. Alternatively, the control processing unit 406 may be incorporated in the detector 402. In this case, high-speed processing can be achieved.

The X-ray measuring instrument in accordance with the present invention may have a filter 410 interposed between the X-ray source 401 and detector 402. The filter 410 is made of a metal such as aluminum, copper, or brass, a ceramic, or a resin. According to the simplest procedure, the filter 410 can be realized with a liquid poured into a case made of plastic or a resin. The filter may have any shape, and a data correction process to be described later can be adapted to any filter shape.

EMBODIMENT 1

The first embodiment of the present invention will be described below.

The control processing unit 406 employed in the present invention executes a process for compensating the non-uniformity in values of a three-dimensional image. The control processing unit 406 internally includes a memory unit 409 and stores in the memory unit 409 a table or the like needed for the compensation process. As an input means for the control processing unit 406, keystroke on a keyboard, reading from a file, and exchanging memory chips are conceivable. The control processing unit 406 supports as an operation menu a mode in which whether the compensation process is executed is entered, or includes switches.

A procedure of compensating the non-uniformity in values of a three-dimensional image will be described below.

(1) Gain data acquisition: X-rays are irradiated in a state, in which a subject is not placed in position, in order to perform measurement, and gain data produced by the detector is acquired.

(2) Offset correction: measurement is performed without X-irradiation in order to acquire offset data produced by the detector. Rotational measurement is performed with a subject placed in position in order to acquire multiple subject data items along with the progress of rotation. The offset data is subtracted from each subject data in order to obtain offset-corrected subject data.

(3) Gain correction: the offset data is subtracted from gain data in order to obtain offset-corrected gain data. The offset-corrected subject data is divided by the offset-corrected gain data in order to obtain gain-corrected subject data.

(4) Logarithmic conversion: logarithmic conversion is performed on the gain-corrected subject data in order to multiply the gain-corrected subject data by −1, whereby projection data is produced.

(5) Non-uniformity compensation: the projection data is multiplied by correction coefficients G in order to obtain non-uniformity-compensated data.

(6) Three-dimensional data acquisition: after the foregoing processing has been performed on all the subject data items, reconstructive computation is performed in order to produce three-dimensional data.

FIG. 1 is a flowchart describing a non-uniformity compensation process employed in the embodiment 1. FIG. 2 shows a conversion lookup table A employed in the non-uniformity compensation process in the embodiment 1. FIG. 3 shows a conversion lookup table B employed in the non-uniformity compensation process in the embodiment 1.

A coordinate in a lateral direction in projection data and a coordinate in a longitudinal direction therein shall be u and v respectively. A position v is specified in projection data As(u,v) of a subject (step 101). A position u is specified in the projection data As(u,v) of the subject (step 102). The conversion lookup table A is searched based on the coordinates (u,v) in order to obtain an X-ray absorption Af(u,v) of the filter (step 103). An equivalent filter thickness Ef(u,v) is calculated as the thickness of the filter, which is equivalent to the filter X-ray absorption Af(u,v), by applying a conversion expression A (described later) to the filter X-ray absorption Af(u,v) (step 104).

A conversion lookup table B is searched based on the calculated equivalent filter thickness Ef(u,v) and subject projection data As(u,v) in order to obtain a correction coefficient G(Ef,As) (step 105). If the expected equivalent filter thickness Ef(u,v) and subject projection data As(u,v) are not found in the conversion lookup table B, approximate values are used to interpolate or extrapolate the correction coefficient G(Ef, As). The subject projection data As(u,v) is multiplied by the correction coefficient G(Ef,As) (step 106). The foregoing procedure is executed for all coordinates u (step 107). The procedure is executed for all coordinates v (step 108). The procedure is executed for all subject projection data items (step 109).

A way of producing the conversion lookup table A shown in FIG. 2 will be described below. X-rays are irradiated with the filter 410, which is employed in measuring a subject, disposed but with the subject unplaced, whereby measurement data is acquired. The aforesaid offset correction, gain correction, and logarithmic conversion are performed on the measurement data in order to produce projection data. A value at coordinates (u,v) in the projection data shall be regarded as an X-ray absorption Af(u,v) of the filter. The coordinate u in the lateral direction in the projection data is changed from 1 to a maximum value Nu, and the coordinate v in the longitudinal direction is changed from 1 to a maximum value Nv. The X-ray absorptions Af(u,v) at the respective coordinate pairs (u,v) are detected and recorded in a lookup table.

In the above pieces of processing, the employment of projection data obtained by averaging projection data items acquired under the same conditions could reduce statistical noise and improve precision.

In the conversion lookup table A, coordinates may be recorded in steps of several points, and an X-ray absorption at any coordinate pair may be calculated by performing interpolation. In this case, the storage capacity of the lookup table can be reduced.

The conversion lookup table A may be held as a conversion expression according to which an X-ray absorption is calculated using coordinates as variables. In this case, the storage capacity of the lookup table can be reduced.

A way of defining a conversion expression A will be described below. X-rays are irradiated with the filter 410 having a predetermined even thickness Ef disposed but with a subject unplaced, whereby measurement data is acquired. The aforesaid offset correction, gain correction, and logarithmic conversion are performed on the measurement data in order to produce projection data. A mean value of the projection data is calculated and regarded as an X-ray absorption Af of the filter 410. Multiple filters whose thicknesses are different from one another are prepared as the filter 410. The filters having different thicknesses are used to acquire projection data items. X-ray absorptions Af are then obtained in association with the respective filter thicknesses Ef. The filter thicknesses Ef associated with the respective X-ray absorptions Af are approximated according to an expression (1) in order to obtain coefficients $a_0$, $a_1$, $a_2$, etc.

[Formula 1]

$$Ef = a_0 + a_1 \cdot A_f + a_2 \cdot A_f^2 + a_3 \cdot A_f^3 \quad (1)$$

A way of producing the conversion lookup table B shown in FIG. 3 will be described below. X-rays are irradiated with the filter 410, which has a predetermined even thickness Ef, disposed and with an arbitrary subject placed in position, whereby measurement data is acquired. Herein, as the arbitrary subject, a cylindrical container or an elliptically cylindrical container filled with water or an acrylic cylinder is adopted. The aforesaid offset correction, gain correction, and logarithmic conversion are performed on the measurement data in order to produce projection data As(u,v). Projection data Ao(u,v) of an ideal subject providing uniform values for a reconstructed image is defined. At each coordinate pair (u,v), the ideal projection data Ao(u,v) is divided by subject projection data As(u,v) in order to work out a correction coefficient G(Ef,As). Multiple filters whose thicknesses are different from one another are prepared as the filter 410. Projection data items of the same arbitrary subject are acquired using the filters having different thicknesses Ef, and correction coefficients G(Ef,As) are calculated for subject projection data As associated with each of the filter thicknesses Ef. The correction coefficients G(Ef,As) for the subject projection data As are approximated using an expression (2) in order to work out coefficients $b_0$, $b_1$, $b_2$, etc.

[Formula 2]

$$G = b_0 + b_1 \cdot A_s + b_2 \cdot A_s^2 + b_2 \cdot A_s^3 \quad (2)$$

For the multiple filters having different thicknesses, the filter thickness Ef is changed from 0 to a maximum value Emax. The subject projection data As is changed from 0 to a maximum value Smax. The approximate expression (2) is used to work out the correction coefficients G(Ef,As), and the correction coefficients are recorded in a lookup table.

In the foregoing pieces of processing, the employment of projection data produced by averaging projection data items obtained under the same conditions could reduce statistical noise and improve precision in calculating a correction coefficient.

In the conversion lookup table B, a filter thickness and subject projection data may be recorded in steps of several points, and a correction coefficient may be calculated by performing interpolation. In this case, the storage capacity of the lookup table can be reduced.

The conversion lookup table B may be held as a conversion expression according to which a correction coefficient is calculated using a filter thickness and subject projection data as variables. In this case, the storage capacity of the lookup table can be reduced.

FIGS. 5A to 5C show three examples of a section of the filter 410 along a plane of rotation of the X-ray source 401 (on the left side) and a perspective view (on the right side). FIG. 5A includes the sectional view and perspective view of the filter 410 having an even thickness. FIG. 5B includes the sectional view and perspective view of the filter 410 that includes a combination of a region having a concave surface and a region having an even thickness. FIG. 5C includes the sectional view and perspective view of the filter 410 that includes a combination of a region having a concave surface, a region having a convex surface, and a region having an even thickness. In the sectional views, a word "X-rays" accompanied by an arrow indicates an incident direction of X-rays. The incident direction of X-rays may be opposite to the direction pointed by the arrow. As shown in FIGS. 5A to 5C, when a filter has a laterally symmetrical shape, the X-ray absorptions in the filter are laterally symmetrical with respect to the filter center. The number of arithmetic operations needed to calculate the absorptions and the storage capacity of the lookup table A can be halved. When the shape of a section of the filter is identical in a depth direction, the X-ray absorptions in the filter are the same in every section. The number of arithmetic operations needed to calculate the absorptions can be decreased and the storage capacity of the lookup table A can be reduced.

FIGS. 6A to 6C are sectional views and a plan view showing another shape of the filter 410. FIG. 6B is the plan view in which the filter is seen in the incident direction of X-rays. FIG. 6A is the sectional view in which the filter is seen at an A-A position in an arrow-pointed direction. FIG. 6C is the sectional view in which the filter is seen at a B-B position in an arrow-pointed direction. As shown in FIG. 6A, the filter 410 includes at the A-A position thereof a combination of a region having a concave surface and a region exhibiting a certain value. At the B-B position, the thickness of the upper part of the filter varies.

When the filter is seen in the X-ray incident direction, the filter shape is identical to the one shown in FIG. 6B. The A-A section of the filter includes, similarly to that shown in FIG. 5C, a combination of a region having a convex surface and a region having an even thickness. On the B-B section of the filter, the thickness of the upper part thereof varies. The border between the region having the concave surface and the region having the even thickness may have a convex shape.

The filter 410 shown in FIG. 5A will prove effective in a case where a subject is relatively flat in a measurement area (detectable area of the detector 402) and measurement is performed while the saturation of the detector 402 is averagely prevented. The filters 410 shown in FIGS. 5B and 5C will prove effective in a case where the thickness of a subject abruptly decreases at both ends of the measurement area. The example shown in FIG. 6 will prove effective in a case where the thickness of a subject abruptly decreases even in the upper part of the measurement area.

To be more specific, the section of the filter 410 shown in FIG. 5C has convex arcs adjoining a concave arc, and has a straight line adjoining each of the convex arcs. When tangents at points of intersections between the concave arc and convex arcs have the same slope and tangents at the points of intersections between the convex arcs and the straight lines have the same slope, the filter permits production of an excellent three-dimensional image of the head, abdomen, inferior limb, or any other human shape. Further, according to the example shown in FIG. 6, when the thickness of the filter varies in the direction of the center axis of rotation of the rotating unit, the filter permits production of an excellent three-dimensional image of the head or any other object shaped to have different thicknesses in a body-axis direction.

According to the embodiment 1, a mean value of projection data produced by disposing a filter, which has a predetermined even thickness, without placing an object in position is calculated. Multiple filters having different thicknesses are used to obtain respective mean values. A polynomial is defined in order to approximate the mean values associated with the filter thicknesses. A conversion expression defining the relationship between the X-ray absorption of a filter and the thickness thereof is produced. Thus, correction can be achieved relative to a filter having an arbitrary thickness.

Moreover, according to the embodiment 1, projection data is produced by disposing a filter, which has a predetermined even thickness, with an arbitrary subject placed in position. Projection data of an ideal object providing uniform values for a reconstructed image is defined. The ideal projection data is divided by the object projection data in order to calculate correction coefficients. Multiple filters having different thicknesses are used to obtain correction coefficients. A conversion lookup table specifying the relationship among the thicknesses of the filters, projection data items of the object, and correction coefficients is produced. Thus, correction can be performed relative to an object having an arbitrary shape.

Moreover, when the aforesaid embodiment 1 is developed, projection data is produced in a state in which: a filter having an arbitrary shape is disposed in place of a filter having an even thickness; and an object is not placed in position. A coordinate in a lateral direction in the projection data and a coordinate in a longitudinal direction therein are changed in order to obtain projection data values at respective coordinate pairs. Consequently, a conversion lookup table specifying the relationship between the projection data values of the object and the X-ray absorptions in the filter is produced. Thus, correction can be achieved relative to the filter having the shape.

Moreover, when the aforesaid embodiment 1 is developed, projection data is produced in a state in which: a filter having an arbitrary shape is disposed in place of a filter having an even thickness; and an arbitrary subject is place in position. Projection data of an ideal object providing uniform values for a reconstructed image is defined. The ideal projection data is divided by the projection data of the object in order to calculate a correction coefficient. The correction coefficient is calculated relative to multiple filters having different thicknesses. A conversion table specifying the relationship among the thicknesses of the filters, projection data items of the object, and correction coefficients is produced. Thus, correction can be achieved for an object, which has an arbitrary shape, using the filter having the shape.

Moreover, according to the embodiment 1, when a water cylinder or elliptical water cylinder is adopted as an arbitrary subject, an object can be simulated readily and precisely. Thus, correction coefficients may be obtained.

ANOTHER EMBODIMENT

For correction employed in the aforesaid embodiment 1, one conversion lookup table and one conversion expression are prepared. In another embodiment, multiple conversion lookup tables and conversion expressions may be prepared in association with radiographic conditions including an X-ray tube voltage, a scattered X-rays shielding grid, and a collimator. In this case, the control processing unit 406 stores the sets of conversion tables and conversion expressions, selects any conversion table and conversion expression according to the radiographic condition, and uses them for correction. The employment of the conversion table and conversion expression associated with the radiographic condition permits improvement of precision in correction. In a still another embodiment, multiple conversion tables and conversion expressions may be selected from among the stored sets of conversion tables and conversion expressions according to a radiographic condition. Interpolation or extrapolation may then be performed in order to calculate correction coefficients suitable for an arbitrary radiographic condition, and the correction coefficients may be used for correction. Thus, highly precise correction can be realized relative to an arbitrary radiographic condition.

INDUSTRIAL APPLICABILITY

According to the present invention, there is provided an X-ray measuring instrument capable of producing an excellent three-dimensional image that is unaffected by a saturation phenomenon in X-ray detector elements, a change in an energy distribution caused by a filter or a subject, or scattered X-rays caused by the filter or subject, and that has the uniformity in values improved by suppressing the saturation of a detector.

BRIEF DESCRIPTION OF THE DRAWINGS

FIG. 2 shows a conversion lookup table A employed in the non-uniformity compensation process of the embodiment 1;

FIG. 3 shows a conversion lookup table B employed in the non-uniformity compensation process of the embodiment 1;

FIG. 4 is a conceptual diagram showing in a sectional form a side view of an example of an X-ray measuring instrument to which the present invention is applied;

FIGS. 5A to 5C show three examples of a section of a filter 410 (on the left side) along a plane of rotation of an X-ray source 401 and a perspective view (on the right side) thereof, FIG. 5A includes the sectional view and perspective view of the filter 410 having an even thickness, FIG. 5B includes the sectional view and perspective view of the filter 410 including a combination of a region which has a concave surface and a region which has an even thickness, and FIG. 5C includes the sectional view and perspective view of the filter 410 including a combination of a region which has a concave surface, a region which has a convex surface, and a region which has an even thickness; FIG. 6B is the plan view in which the filter 410 is seen in an X-ray incident direction, FIG. 6A is the sectional view in which the filter 410 is seen at an A-A position thereof in an arrow-pointed direction, and FIG. 6C is the sectional view in which the filter 410 is seen at a B-B position thereof in an arrow-pointed direction.

DESCRIPTION OF REFERENCE NUMERALS

Figure 1:
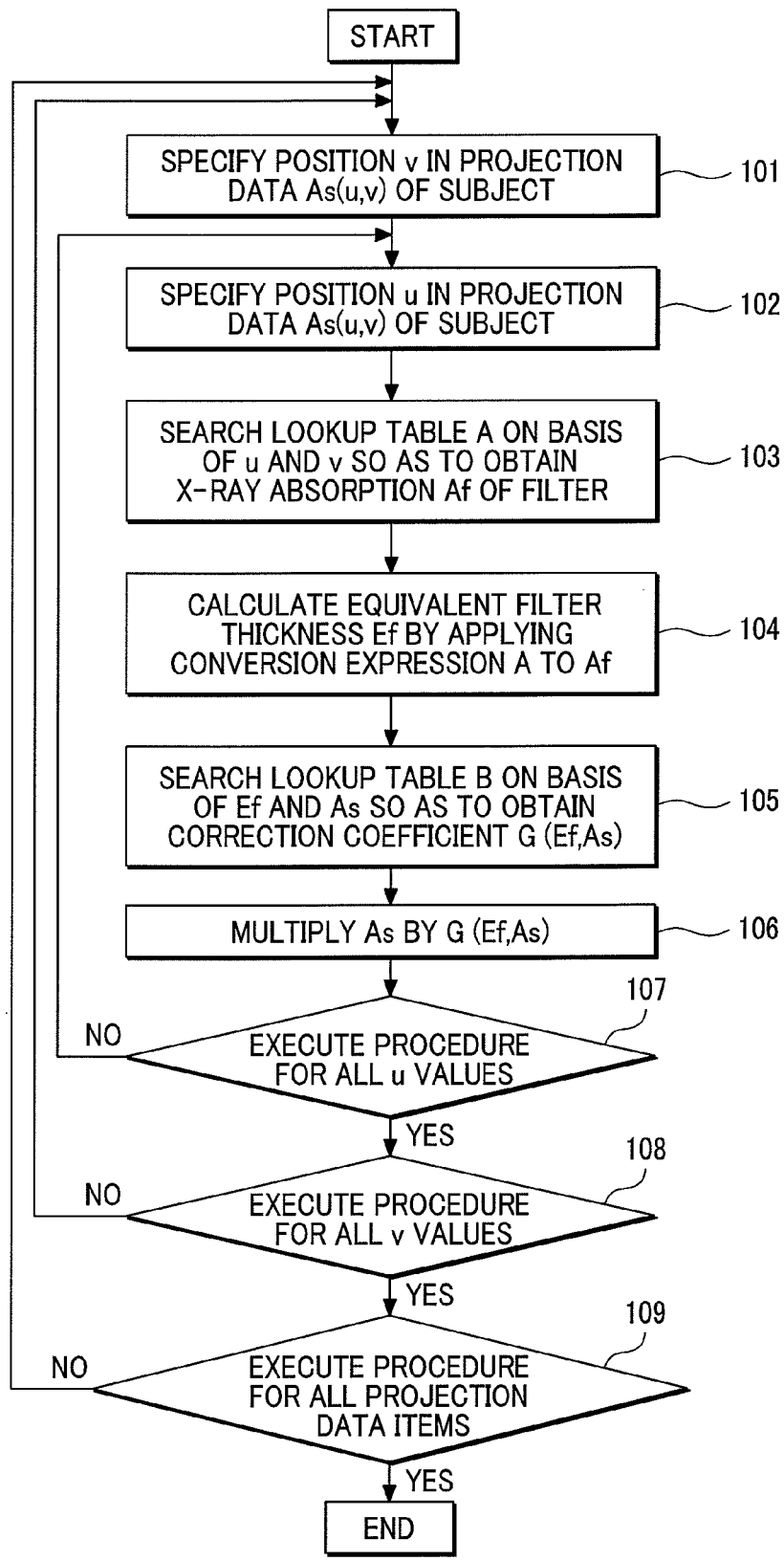
FIG. 1 is a flowchart describing a procedure in a non-uniformity compensation process of an embodiment 1.
Figure 6A:
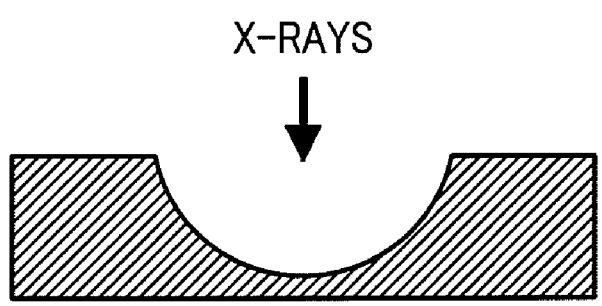
FIGS. 6A to 6C are sectional views and a plan view showing another shape of the filter 410.
Figures 6B, 6C:
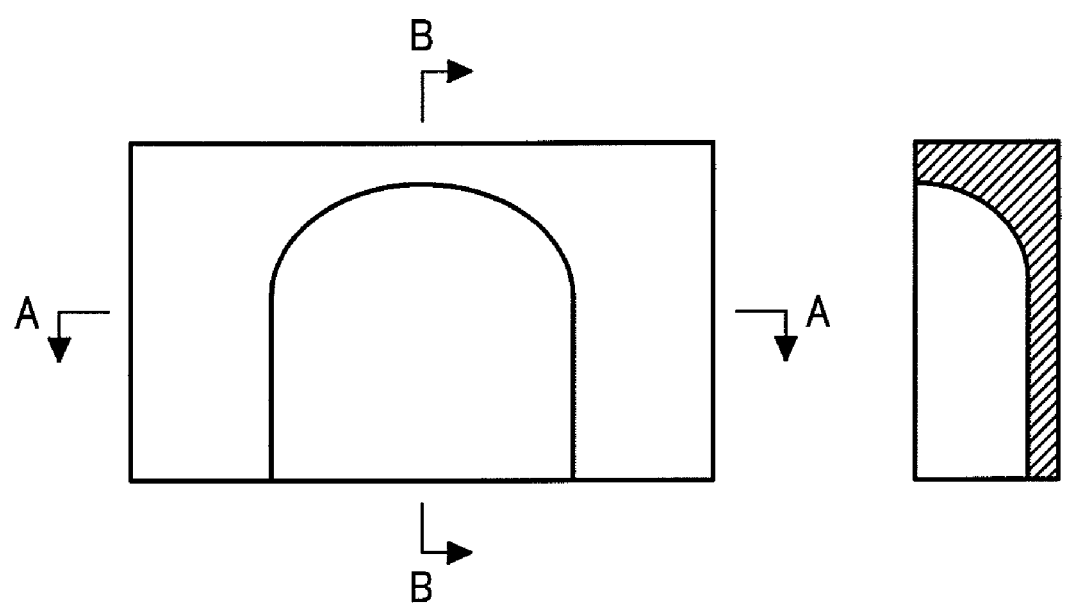

401: X-ray source, 402: detector, 403: support, 404: rotating unit, 405: table, 406: control processing unit, 407: axis of rotation, 408: subject, 409: memory unit, 410: filter.

The invention claimed is:

1. An X-ray measuring instrument comprising: an X-ray source that generates X-rays to be irradiated to an object; an X-ray detector that is opposed to the X-ray source with the subject between them and detects X-rays transmitted by the object as measurement data; a filter that is interposed between the X-ray source and the object and regulates an exposure of X-rays to be transmitted; a holding unit that holds the X-ray source and the X-ray detector; a rotating unit that rotates the X-ray source and the X-ray detector about the object; and a control processing unit that computes measurement data items which are detected by the X-ray detector at a plurality of angles with respect to the object rotated by the rotating unit; wherein, the control processing unit logarithmically converts the measurement data so as to produce projection data, obtains an X-ray absorption coefficient relevant to the filter using the produced projection data, calculates the thickness of the filter by applying a predetermined conversion expression to the obtained X-ray absorption coefficient, obtains a correction coefficient for the produced projection data according to the calculated thickness of the filter, multiplies the projection data by the obtained correction coefficient, computes the projection data, which is multiplied by the correction coefficient, for reconstruction, and thus produces a three-dimensional image.

2. The X-ray measuring instrument according to claim 1, wherein the control processing unit searches a first conversion lookup table on the basis of the projection data so as to obtain the X-ray absorption of the filter.

3. The X-ray measuring instrument according to claim 1, wherein the first conversion lookup table is produced in such a manner that: prior to measurement of the object, measurement data is obtained in a state in which the filter is disposed but the object is not placed in position; the measurement data is logarithmically converted in order to produce projection data; a coordinate in a lateral direction in the projection data and a coordinate in a longitudinal direction therein are changed in order to obtain projection data values at respective coordinate pairs; and the relationship between the projection data values of the object and the X-ray absorptions in the filter is defined.

4. The X-ray measuring instrument according to claim 1, wherein the control processing unit searches a second conversion lookup table on the basis of the projection data so as to obtain the correction coefficient.

5. The X-ray measuring instrument according to claim 1, wherein the second conversion lookup table is produced in such a manner that: measurement data is obtained in a state in which a filter having a predetermined even thickness is disposed and an arbitrary subject is placed in position; projection data is produced by logarithmically converting the measurement data; projection data of an ideal object providing uniform values for a reconstructed image is defined; a correction coefficient is calculated by dividing the ideal projection data by the projection data of the object; the correction coefficient is obtained relative to a plurality of filters having different thicknesses; and the relationship among the thicknesses of the filters, the projection data items of the object, and the correction coefficients is defined.

6. The X-ray measuring instrument according to claim 1, wherein for obtaining the X-ray absorptions of the filter, the control processing unit uses projection data produced by averaging projection data items obtained under the same conditions.

7. The X-ray measuring instrument according to claim 2, wherein for obtaining the X-ray absorptions of the filter, the control processing unit records a coordinate pair in the first conversion table in steps of several points, and calculates an X-ray absorption at an arbitrary coordinate pair by performing interpolation.

8. The X-ray measuring instrument according to claim 2, wherein for obtaining the X-ray absorption of the filter, the control processing unit holds the second conversion lookup table as a conversion expression according to which an X-ray absorption is calculated using coordinates as variables, and calculates the X-ray absorption according to the conversion expression.

9. The X-ray measuring instrument according to claim 1, wherein for obtaining the thickness of the filter, the control processing unit uses projection data produced by averaging projection data items obtained under the same conditions.

10. The X-ray measuring instrument according to claim 4, wherein for obtaining the thickness of the filter, the control processing unit records a coordinate pair in the second conversion lookup table in steps of several points, and calculates an X-ray absorption at an arbitrary coordinate pair by performing interpolation.

11. The X-ray measuring instrument according to claim 4, wherein for obtaining the thickness of the filter, the control processing unit holds the second conversion lookup table as a conversion expression according to which an X-ray absorption is calculated using coordinates as variables, and calculates the X-ray absorption according to the conversion expression.

12. The X-ray measuring instrument according to claim 1, wherein the shape of the filter is laterally symmetrical.

13. The X-ray measuring instrument according to claim 1, wherein the shape in a depth direction of a section of the filter is identical.

14. The X-ray measuring instrument according to claim 1, wherein the shape of a section of the filter has convex arcs adjoining a concave arc and has straight lines adjoining the respective convex arcs, the tangents at the points of intersections between the concave arc and the convex arcs have the same slope, and the tangents at the points of intersections between the convex arcs and the straight lines have the same slope.

15. The X-ray measuring instrument according to claim 1, wherein the thickness of the filter varies in the direction of the center axis of rotation of the rotating unit.

16. The X-ray measuring instrument according to claim 1, wherein the control processing unit has a correction coefficient obtained from the projection data of an arbitrary subject formed as a water cylinder or an elliptic water cylinder.

17. The X-ray measuring instrument according to claim 1, wherein the control processing unit selects a correction coefficient from among a plurality of correction coefficients according to a radiographic condition under which the object is radiographed.

* * * * *